US007570171B2

(12) United States Patent
Kimoto et al.

(10) Patent No.: US 7,570,171 B2
(45) Date of Patent: Aug. 4, 2009

(54) RECEIVING APPARATUS

(75) Inventors: Seiichiro Kimoto, Hachioji (JP);
Toshiaki Shigemori, Hachioji (JP);
Manabu Fujita, Hino (JP); Akira Matsui, Hino (JP); Kazutaka Nakatsuchi, Hino (JP); Ayako Nagase, Hachioji (JP)

(73) Assignee: Olympus Corporation (JP)

( * ) Notice: Subject to any disclaimer, the term of this patent is extended or adjusted under 35 U.S.C. 154(b) by 360 days.

(21) Appl. No.: 11/573,430

(22) PCT Filed: Aug. 18, 2006

(86) PCT No.: PCT/JP2006/316268

§ 371 (c)(1),
(2), (4) Date: Feb. 8, 2007

(87) PCT Pub. No.: WO2007/021009

PCT Pub. Date: Feb. 22, 2007

(65) Prior Publication Data

US 2009/0002177 A1    Jan. 1, 2009

(30) Foreign Application Priority Data

Aug. 19, 2005    (JP) .............................. 2005-238657

(51) Int. Cl.
*G08B 23/00*    (2006.01)

(52) U.S. Cl. .............................. 340/573.1; 340/539.12; 340/572.1; 600/300; 600/118

(58) Field of Classification Search .............. 340/573.1, 340/539.1, 539.11, 539.12, 505, 999, 572.1, 340/500; 600/117, 118, 103, 160, 300, 301
See application file for complete search history.

(56) References Cited

U.S. PATENT DOCUMENTS 5,483,969 A * 1/1996 Testerman et al. .......... 600/529
5,951,462 A * 9/1999 Yamanaka .................. 600/118

FOREIGN PATENT DOCUMENTS

| EP | 1 702 554 | 9/2006 |
| JP | 7-160458 | 6/1995 |
| JP | 11-169338 | 6/1996 |
| JP | 2003-019111 | 1/2003 |
| JP | 2005-223427 | 8/2005 |

* cited by examiner

*Primary Examiner*—Eric M Blount
(74) *Attorney, Agent, or Firm*—Ostrolenk, Faber, LLP

(57) ABSTRACT

The invention provides a receiving apparatus that can suppress data loss when an antenna is detached. When a non-connection of an antenna is detected (step S103: Yes) after a recording operation is started (step S101: Yes), the receiving apparatus operates a warning unit to issue a warning to a user to the effect that the antenna is detached (step S105). Therefore, the receiving apparatus does not issue a warning (step S102) when there is no problem even when the antenna is detached, such as when an examination is not yet started (step S101: No). When the antenna is detached in a state that the use of the antenna is essential during an examination, the receiving apparatus notifies the user such as a subject about this fact, thereby prompting the user to correct the connection of the antenna. As a result, the data loss when the antenna is detached can be suppressed.

20 Claims, 6 Drawing Sheets

RECEIVING APPARATUS

CROSS REFERENCE TO RELATED APPLICATION

The present application is a 35 U.S.C. §§ 371 national phase conversion of PCT/JP2006/316268, filed 18 Aug. 2006, which claims priority of Japanese Patent Application No. 2005-238657 filed 19 Aug. 2005, which is herein, incorporated by reference.

TECHNICAL FIELD

The present invention relates to a receiving apparatus that receives a radio signal transmitted from a body-insertable apparatus such as a capsule endoscope inserted into a subject, using an antenna at the outside of the subject.

BACKGROUND ART

In recent years, in the field of endoscope, a capsule endoscope having an imaging function and a radio communication function has appeared. After a subject swallows the capsule endoscope from the mouth to perform an observation (examination), the capsule endoscope moves within internal organs (within the body cavity) such as an esophagus, a stomach, and a small bowel, following its peristalsis, during the observation period, until when the capsule endoscope is naturally discharged from the body (human body) of the subject. The capsule endoscope sequentially images at a predetermined imaging rate, using the imaging function.

During the observation period when the capsule endoscope moves within the internal organs, image data acquired by imaging within the body cavity by the capsule endoscope is sequentially transmitted to the outside of the subject, by the radio communication function such as radio transmission, and is stored into a memory provided within an external receiving device. When the subject carries the receiving device having the radio communication function and the memory function, the subject can move freely even during the observation period from when the subject swallows the capsule endoscope until when the capsule endoscope is discharged. After the observation, a doctor or a nurse can perform diagnosis by displaying the images of the body cavity on a display unit such as a display, based on image data stored in the memory of the receiving device (see Patent Document 1).

In receiving image data, in general, a receiving device has plural antennas dispersedly disposed at the outside of the subject to receive image signals transmitted from the capsule endoscope, and receives an image signal by selectively switching one antenna having large reception strength. For example, the Patent Document 1 describes a receiving device that switches reception of plural antennas disposed at the outside of the subject, and searches a position of the capsule endoscope within the subject as a signal source of an image signal, based on field strength that each antenna receives.

Patent Document 1: Japanese Patent Application Laid-open No. 2003-19111

DISCLOSURE OF INVENTION

Problem to be Solved by the Invention

An antenna connected to the receiving device has a relatively long cable disposed at the outside of the subject and is connected to the receiving device. Therefore, the antenna can be detached from the receiving device to avoid interruption of the cable when the subject wears the antenna, except during the examination. More specifically, cables that are connected to plural antennas are set as units using a connector, and are detachably connected to the receiving device. After the antennas are disposed at the outside of the subject, the connector of the cables of the antennas is connected to the receiving device, and the examination is started.

During the observation with the capsule endoscope, the subject can move freely by carrying the receiving device. However, the connector of the cables of the antennas can be detached from the receiving device, for some reason. When the antennas are detached, the receiving device cannot receive image data of the body cavity transmitted from the capsule endoscope, and the important body-cavity image data sequentially transmitted for the examination are lost. In other words, the prepared examination using the capsule endoscope becomes wasteful. Conventionally, effective measure against this situation has not been taken.

The present invention has been achieved in view of the above problems. It is an object of the present invention to provide a receiving apparatus that can suppress data loss when antennas are detached.

Means for Solving Problem

A receiving apparatus according to one aspect of the present invention includes: an antenna that is detachably connected to a receiving apparatus main body, and receives a radio signal transmitted from a body-insertable apparatus; an operation start detector that detects a start of a recording operation following a reception of a radio signal transmitted from the body-insertable apparatus; a connection state detector that detects a state of connection of the antenna to the receiving apparatus main body; a warning unit that issues a warning to a user; and a controller that operates the warning unit when a non-connection of the antenna is detected after a recording operation is started.

In the receiving apparatus, the receiving apparatus may further include a measuring unit that measures a lapse time since the recording operation is started, wherein the controller may operate the warning unit when a non-connection of the antenna is detected after the recording operation is started and before a predetermined time set in advance passes.

In the receiving apparatus, the receiving apparatus may further include an external-device connection detector that detects presence of a connection with an external data processor, wherein the controller may operate the warning unit when a non-connection of the antenna is detected in a state that the external data processor is not connected after the recording operation is started.

In the receiving apparatus, the warning unit may issue a warning by displaying a warning on a display unit.

In the receiving apparatus, the warning unit may issue a warning by lighting on or blinking a light-emitting element.

In the receiving apparatus, the warning unit may issue a warning using a warning sound.

In the receiving apparatus, the warning unit may issue a warning by vibrating the receiving apparatus main body.

EFFECT OF THE INVENTION

A receiving apparatus according to the present invention operates a warning unit to warn a user that an antenna is detached, when a non-connection of the antenna is detected after a recording operation is started. Therefore, the receiving apparatus does not issue a warning when detachment of the antenna has no problem such as when an examination is not yet started. The receiving apparatus issues a warning to a user such as a subject, when the antenna is detached in a state that the use of the antenna is essential for the examination or the like. With this arrangement, the user can be prompted to connect the antenna again, thereby suppressing data loss when the antenna is detached.

EXPLANATIONS OF LETTERS OR NUMERALS

Figure 1:
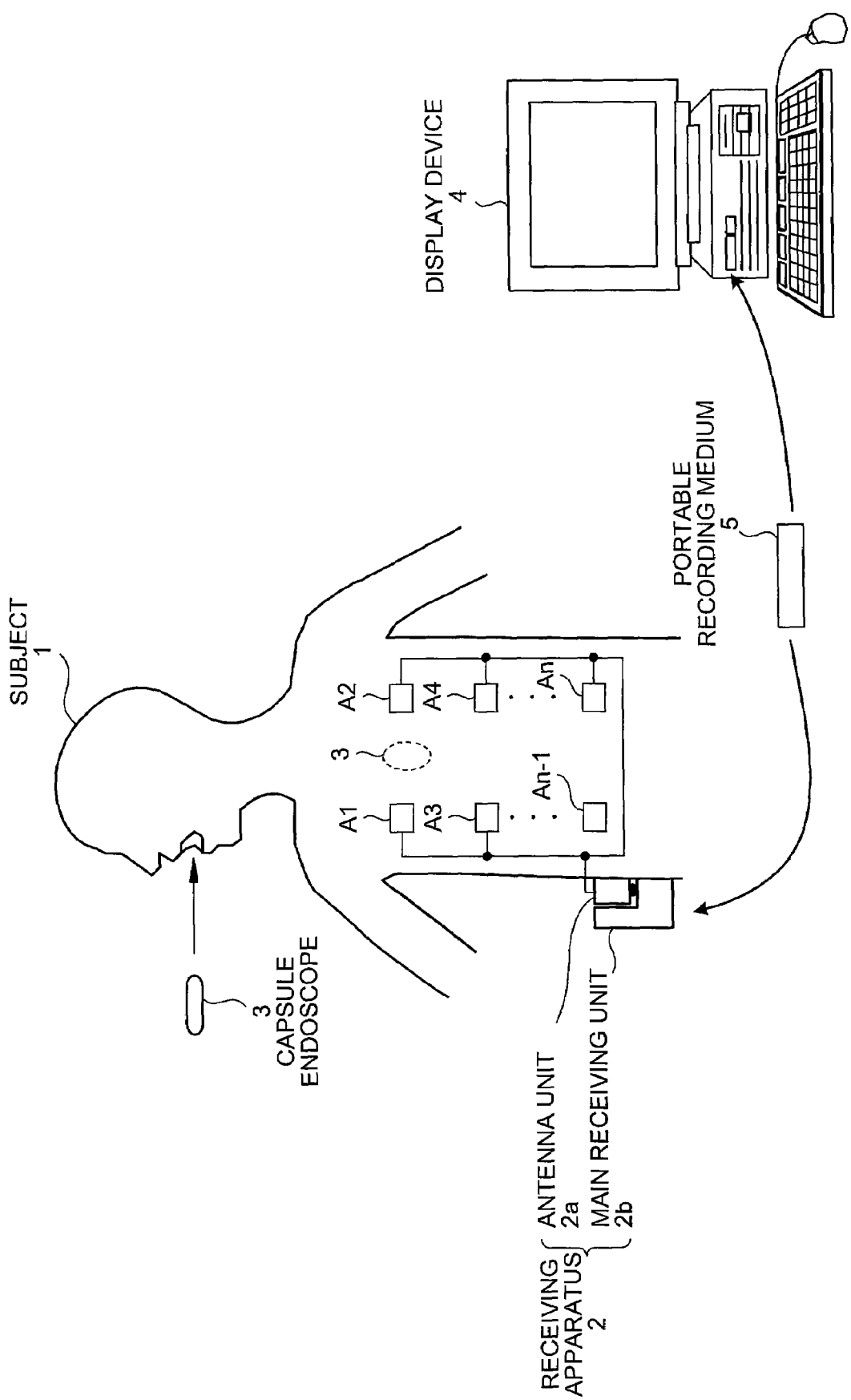
FIG. 1 is a schematic diagram showing an entire configuration of a radio intra-subject information acquiring system according to a first embodiment of the present invention.

1 Subject
2 Receiving apparatus
2a Antenna unit
2b Main receiving unit
3 Capsule endoscope
4 Display device
5 Portable recording medium
15 Display unit
22 Timer

BEST MODE(S) FOR CARRYING OUT THE INVENTION

Exemplary embodiments of a receiving apparatus according to the present invention will be explained below in detail with reference to the accompanying drawings. Note that the invention is not limited to the embodiments, and the embodiments can be variously modified without departing from the scope of the invention.

First Embodiment

FIG. 1 is a schematic diagram showing an entire configuration of a radio intra-subject information acquiring system as a preferred embodiment of a receiving apparatus according to the present invention. The radio intra-subject information acquiring system uses a capsule endoscope as one example of a body-insertable apparatus as a transmitting apparatus. In FIG. 1, the radio intra-subject information acquiring system includes a receiving apparatus 2 that has a radio receiving function, and a capsule endoscope 3 that is inserted into a subject 1, images a body cavity, and transmits an image signal to the receiving apparatus. The radio intra-subject information acquiring system also includes a display device 4 that displays a body-cavity image based on an image signal received by the receiving apparatus 2, and a portable recording medium 5 that delivers data between the receiving apparatus 2 and the display device 4. The receiving apparatus 2 includes an antenna unit 2a that has plural receiving antennas A1 to An adhered to the external surface of the body of the subject 1, and a main receiving unit 2b as a receiving apparatus main body that processes radio signals received via the receiving antennas A1 to An. These units are detachably connected via a connector. The receiving antennas A1 to An can be also fitted to a receiving jacket that the subject can wear. The subject 1 can wear the receiving jacket, thereby fitting the receiving antennas A1 to An. In this case, the receiving antennas A1 to An can be detachable to the jacket.

The display device 4 displays a body cavity image picked up by the capsule endoscope 3, and has a configuration of a workstation that displays an image based on the data acquired by the portable recording medium 5. Specifically, the display device 4 can be configured to directly display an image using a CRT display, a liquid crystal display, or the like, or can be configured to output an image to other medium such a printer.

For the portable recording medium 5, a Compact Flash (registered trademark) memory or the like is used. The portable recording medium 5 is detachable to the main receiving unit 2b and the display device 4, and can output or record information when the portable recording medium 5 is mounted on both. In the present embodiment, the portable recording medium 5 is mounted on the display device 4 of the workstation, and stores identification information such as an examination ID. Immediately before the examination, the portable recording medium 5 is mounted on the main receiving unit 2b. The main receiving unit 2b reads the identification information, and registers the information into the main receiving unit 2b. While the capsule endoscope 3 is moving within the body cavity of the subject 1, the portable recording medium 5 is mounted on the main receiving unit 2b fitted to the subject 1, and records the data transmitted from the capsule endoscope 3. After the capsule endoscope 3 is discharged from the subject 1, that is, after the imaging within the subject 1 ends, the portable recording medium 5 is taken out from the main receiving unit 2b, and is mounted on the display device 4. The display device 4 reads the data recorded on the portable recording medium. For example, the portable recording medium 5 delivers data between the main receiving unit 2b and the display device 4, so that the subject 1 can move freely during the imaging of the body cavity. This arrangement contributes to shorten the period of data delivery to the display device 4. The data can be also delivered between the main receiving unit 2b and the display device 4, using other recording device such as a hard disk incorporated in the main receiving unit 2b. The recording device and the display device 4 can be connected by wire or by radio to deliver data between the both.

Figure 2:
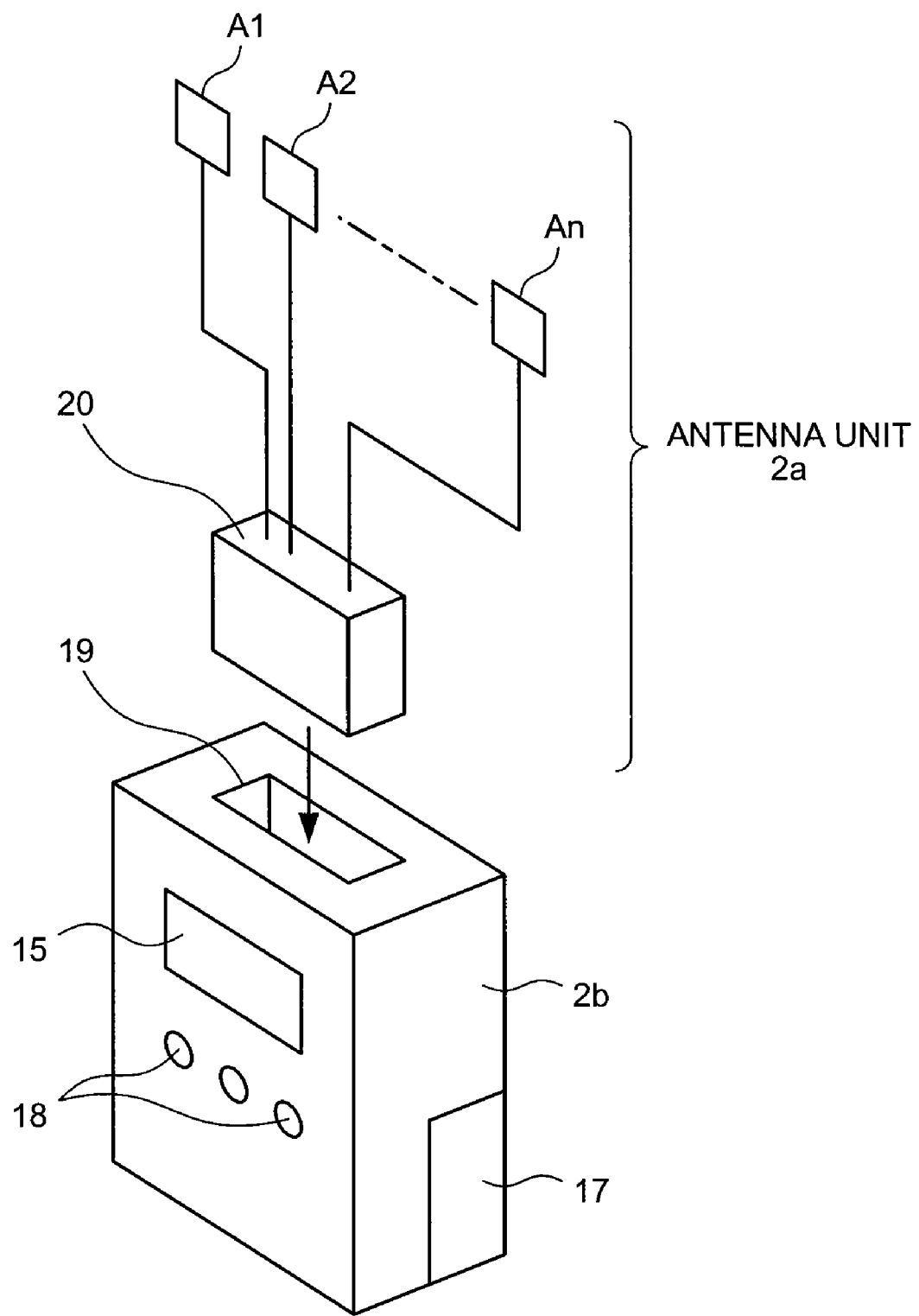
FIG. 2 is a schematic diagram showing an exterior of a receiving apparatus.
Figure 3:
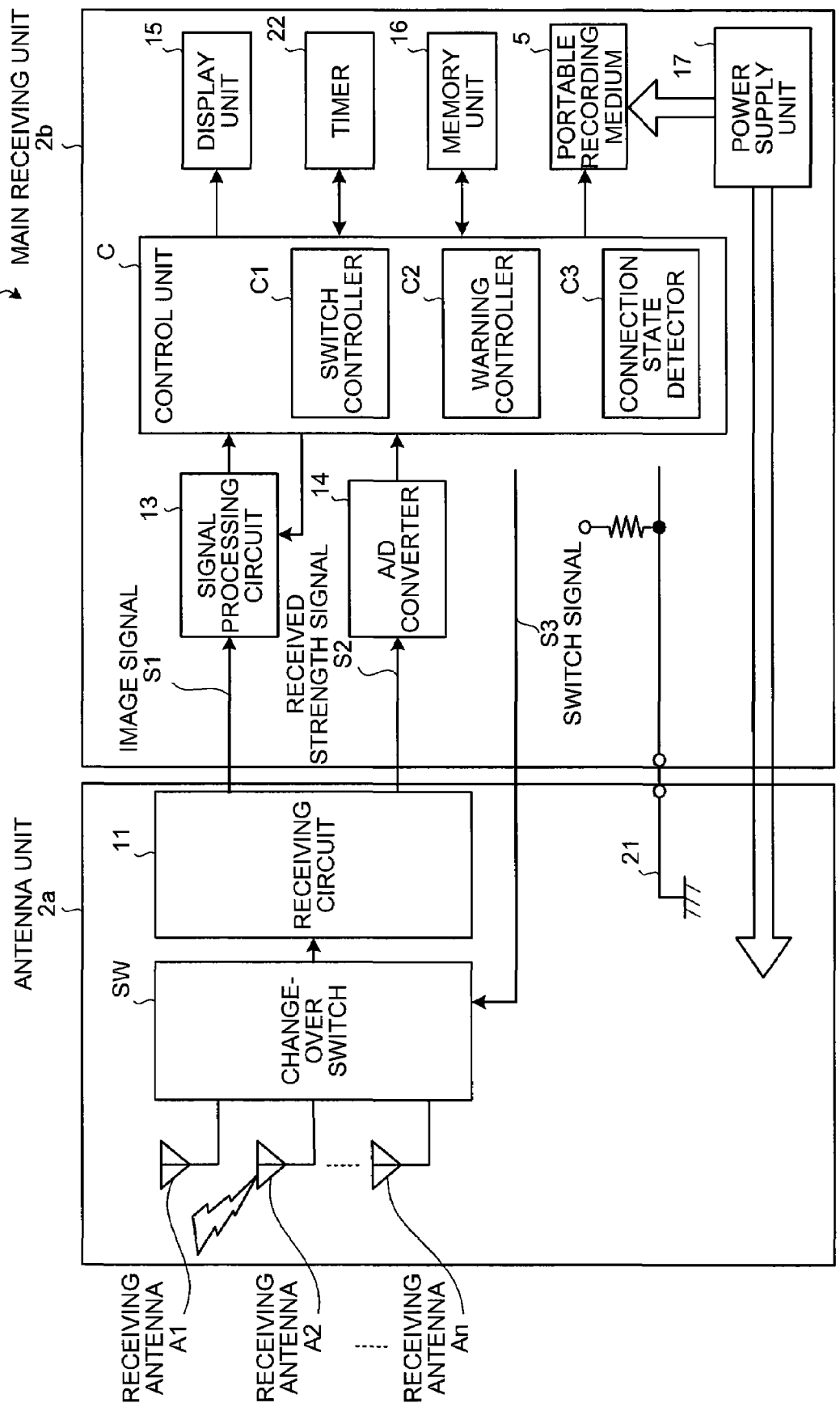
FIG. 3 is a schematic block diagram showing a configuration example of a receiving apparatus.

A configuration of the receiving apparatus is explained below using a schematic diagram of the FIG. 2 and a block diagram of FIG. 3. The receiving apparatus 2 has a function of receiving the image data within the body cavity radio-transmitted from the capsule endoscope 3. As shown in FIG. 2 and FIG. 3, the receiving apparatus 2 has a shape that enables the subject 1 to wear and carry the receiving apparatus 2, and includes the antenna unit 2a and the main receiving unit 2b that is detachably connected to the antenna unit 2a. The antenna unit 2a receives radio signals transmitted from the capsule endoscope 3, via the receiving antennas A1 to An, and demodulates the radio signals into image signals. The main receiving unit 2b performs signal processing of the image signals.

As shown in FIG. 2, a battery pack 17 as a power supply unit that accommodates a power supply battery is detachably fitted to the external surface of the main receiving unit 2b. When the battery pack 17 is mounted on the main receiving unit 2b, the battery and an internal device described later of the main receiving unit 2b are electrically connected, and power can be supplied to the internal device. A display unit 15 as a display including a liquid crystal display such as an LCD and a warning unit is provided in the front external surface, and the display unit 15 displays identification information such as the registered examination ID. An operation switch 18 is provided on the front external surface, thereby making it possible to select information to be displayed on the display unit 15 and adjust a color tone of the display unit 15. An inserting unit no shown of the portable recording medium 5 is provided on the side external surface, thereby detachably holding the inserted portable recording medium 5, and enabling the main receiving unit 2b to record image data. Further, a connecting unit 19 is provided on the upper external surface to detachably connect the cables of the receiving antennas A1 to An. A casing 20 of the antenna unit 2a has a connector not shown that is connected to the connecting unit 19.

As shown in FIG. 3, the antenna unit 2a includes a changeover switch SW that selectively switches one of the receiving antennas A1 to An, and a receiving circuit 11 that is connected to a latter stage of the changeover switch SW, amplifies radio signals from the receiving antennas A1 to An of which connection is switched by the changeover switch SW, and demodulates the amplified radio signals into image signals as transmission information.

The main receiving unit 2b receives an image signal demodulated by the antenna unit 2a, and processes this signal. As shown in FIG. 3, the main receiving unit 2b includes: a signal processing circuit 13 and an A/D converter 14 that are connected to the latter stage of the receiving circuit 11, via the connecting unit 19 and the connector not shown of the casing 20; the display unit 15; a memory unit 16 that stores various information; the portable recording medium 5; a control unit C that controls these constituent elements; and a power supply unit 17 that supplies power to the main receiving unit 2b and the antenna unit 2a.

The signal processing circuit 13 performs processing such as serial-parallel conversion, an image interpolation process, and a compression process on image signal data demodulated by the receiving circuit 11 of the antenna unit 2a. The control unit C includes a switch controller C1 that switches an antenna; a warning controller C2 as a controller that controls whether to display a warning that indicates detachment of an antenna to a user through the display unit 15; and a connection state detector C3 as a connection state detector that detects a state of connection to the connecting unit 19 of the main receiving unit 2b of the casing 20 of the antenna unit 2a.

The receiving circuit 11 amplifies a radio signal output from the changeover switch SW, outputs a demodulated image signal S1 to the signal processing circuit 13, and outputs a received strength signal S2 showing signal strength of the amplified radio signal to the A/D converter 14. The control unit C stores the image data processed by the signal processing circuit 13 into the portable recording medium 5, and displays an image according to need. The control unit C takes in the received strength signal S2 that is converted into a digital signal by the A/D converter 14. The switch controller C1 selects a receiving antenna that receives the digital signal in largest signal strength, as a receiving antenna that acquires image data, based on the received strength signal S2 acquired by sequentially switching the receiving antennas A1 to An. The switch controller C1 outputs a switch signal S3 that instructs a switch to the antenna, to the changeover switch SW. The control unit C stores the signal strength received by each receiving antenna, together with the image data, into the portable recording medium 5, by relating the signal strength to the selected receiving antenna. The stored signal strength of each receiving antenna becomes the information to be used to calculate a position of the capsule endoscope 3 within the subject when the image data is received.

The connection state detector C3 detects whether the casing 20 of the antenna unit 2a is connected to the connecting unit 19 of the main receiving unit 2b. In the present embodiment, a signal line 21 for detecting open-circuit (for detecting an antenna connection) is provided, separately from an RF signal line for the image signal S1 and the received strength signal S2, within the cable of the antenna unit 2a. The connection state detector C3 detects a connection/non-connection (detachment of an antenna), based on a level state of the signal line 21. For example, in the present embodiment, the connection state detector C3 detects that the signal line 21 is in a connection state, when the signal line 21 is at an L level, and detects that the signal line 21 is in a non-connection state (detachment of an antenna), when the signal line 21 is at an H level.

When the connection state detector C3 detects an detachment of an antenna, the warning controller C2 controls the operation of the display unit 15 to issue a warning, in a predetermined condition, using a warning display on the display unit 15 such as "Antenna is detached. Please connect it again."

A predetermined condition of issuing a warning is determined depending on whether the use of the antennas A1 to An is essential, in the flow of an examination executed by the capsule endoscope 3. First, prior to the start of the examination, data of a patient is set to the storage unit 16 of the main receiving unit 2b. Next, the antennas A1 to An are set to predetermined parts of the subject 1. At this stage, even when the antennas A1 to An are not connected to the main receiving unit 2b, the antennas are in a normal state (conversely, the antennas A1 to An can be detached to the main receiving unit 2b, by considering the workability during the operation). Thereafter, the examination is started, by mounting the casing 20 of the antennas A1 to An on the connecting unit 19 of the main receiving unit 2b to set the antennas in a connection state. After the examination is started, the main receiving unit 2b receives body-cavity image data radio-transmitted from the capsule endoscope 3 through the antennas A1 to An, and sequentially records the image data into the portable recording medium 5. When the antenna is detached (when the casing 20 is detached) at this stage for some reason, it is an abnormal state.

Figure 4:
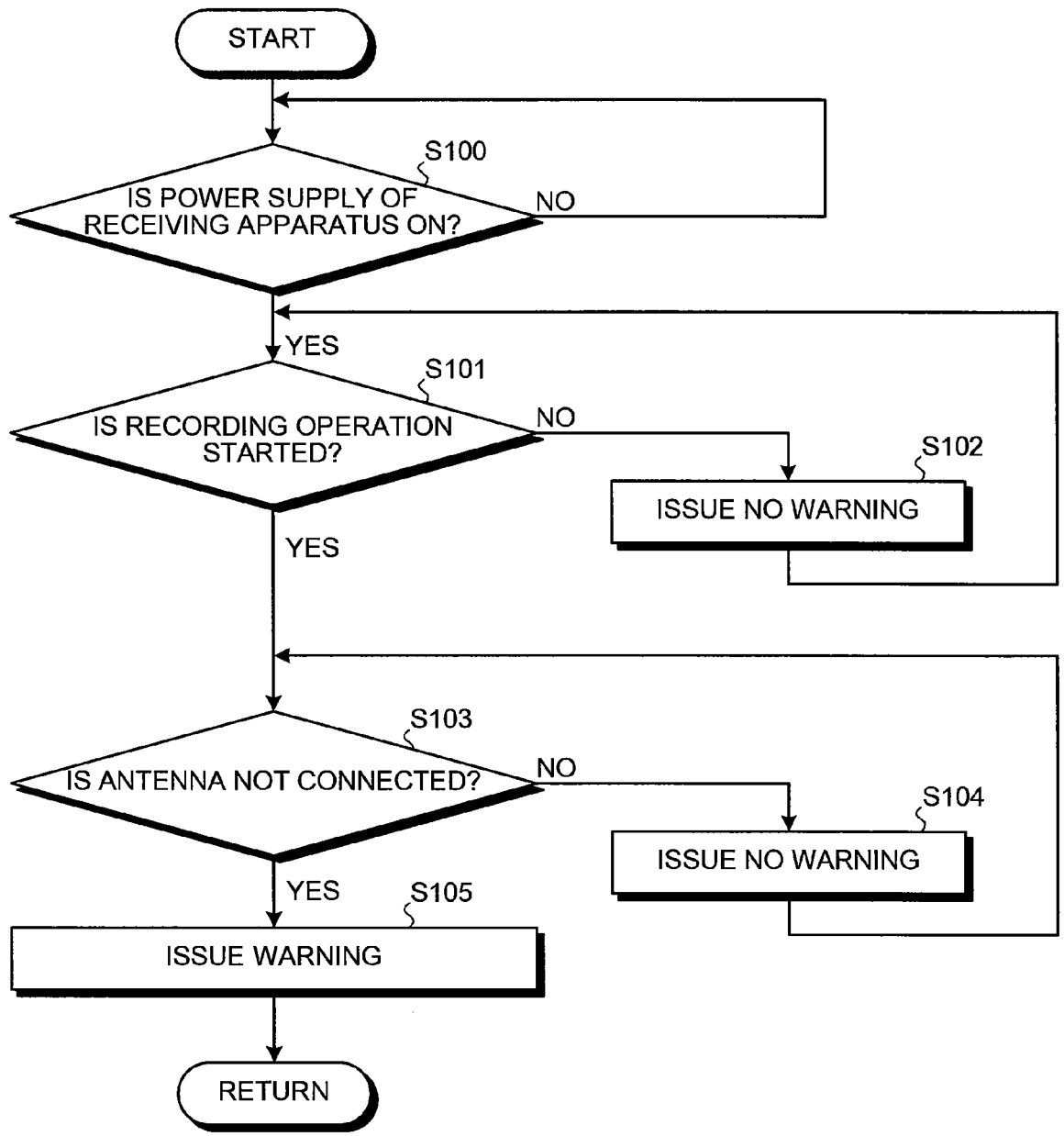
FIG. 4 is a schematic flowchart showing an example of warning control executed when an antenna according to the first embodiment is detached.

In other words, even when the antenna is detached, it is not preferable to issue a warning before starting an examination (before starting acquisition of a body cavity image). In the present embodiment, a warning is issued to notify an abnormal state, when the antenna is detached after the examination, for which the use of the antenna is essential, is started. An example of warning control when the antenna according to the present embodiment is detached is explained with reference to a schematic flow chart shown in FIG. 4. This process is executed in a state that the power supply switch of the receiving apparatus 2 (the main receiving unit 2b) is turned on (step S100: Yes). Next, whether a recording operation is started is determined to determine whether the examination has been started (step S101). As an example of this determination process, it is determined that the recording operation has not been started yet, when a triggering synchronization is not detected from the radio signal transmitted from the capsule endoscope 3 after the power supply is turned on (step S101: No). Once a synchronization signal is detected, it is determined that the recording has been started (step S101: Yes). The portable recording medium 5 is formatted before the examination is started. Therefore, by looking at a state of writing to the portable recording medium 5, it can be determined that the recording operation has not yet been started, when body-cavity image data has not yet been written into the portable recording medium 5. When the recording operation is not yet started (step S101: No), the state is normal even when the antenna is detached, and it is not necessary to warn the user. Therefore, the warning controller C2 controls the display unit 15 not to issue a warning (step S102).

On the other hand, if the recording operation has been already started (step S101: Yes), it is determined whether the casing 20 of the antennas A1 to An is in the non-connection state (the antenna-detached state), by referencing a result of the detection executed by the connection state detector C3 (step S103). When the antenna detachment has not occurred (step S103: No), the state is normal, and no warning is issued to the user. Therefore, the warning controller C2 controls the display unit 15 not to issue a warning (step S104). When the antenna is detached (step S103: Yes), the state is abnormal, and the warning controller C2 controls the operation of the display unit 15 to display the warning of "Antenna is detached. Please connect it again." (step S105). With this arrangement, the user (the subject 1, the doctor, or the nurse) can promptly make proper response to make the connecting unit 19 of the main receiving unit 2b connect the casing 20 of the antennas A1 to An again, thereby suppressing data loss when the antenna is detached.

The order of the determination of the start of the recording operation (step S101) and the determination of the antenna non-connection (step S103) can be opposite so that the determination of the antenna non-connection is executed first. The warning display of the antenna non-connection is not limited to be executed by the display unit 15, and the warning can be issued by lighting on or blinking a light-emitting element such as an LED. Alternatively, a buzzer or a speaker can be used to issue a warning by sound. Alternatively, a vibrator can be incorporated in the main receiving unit 2b, and the main receiving unit 2b can be vibrated to issue a warning.

Second Embodiment

Figure 5:
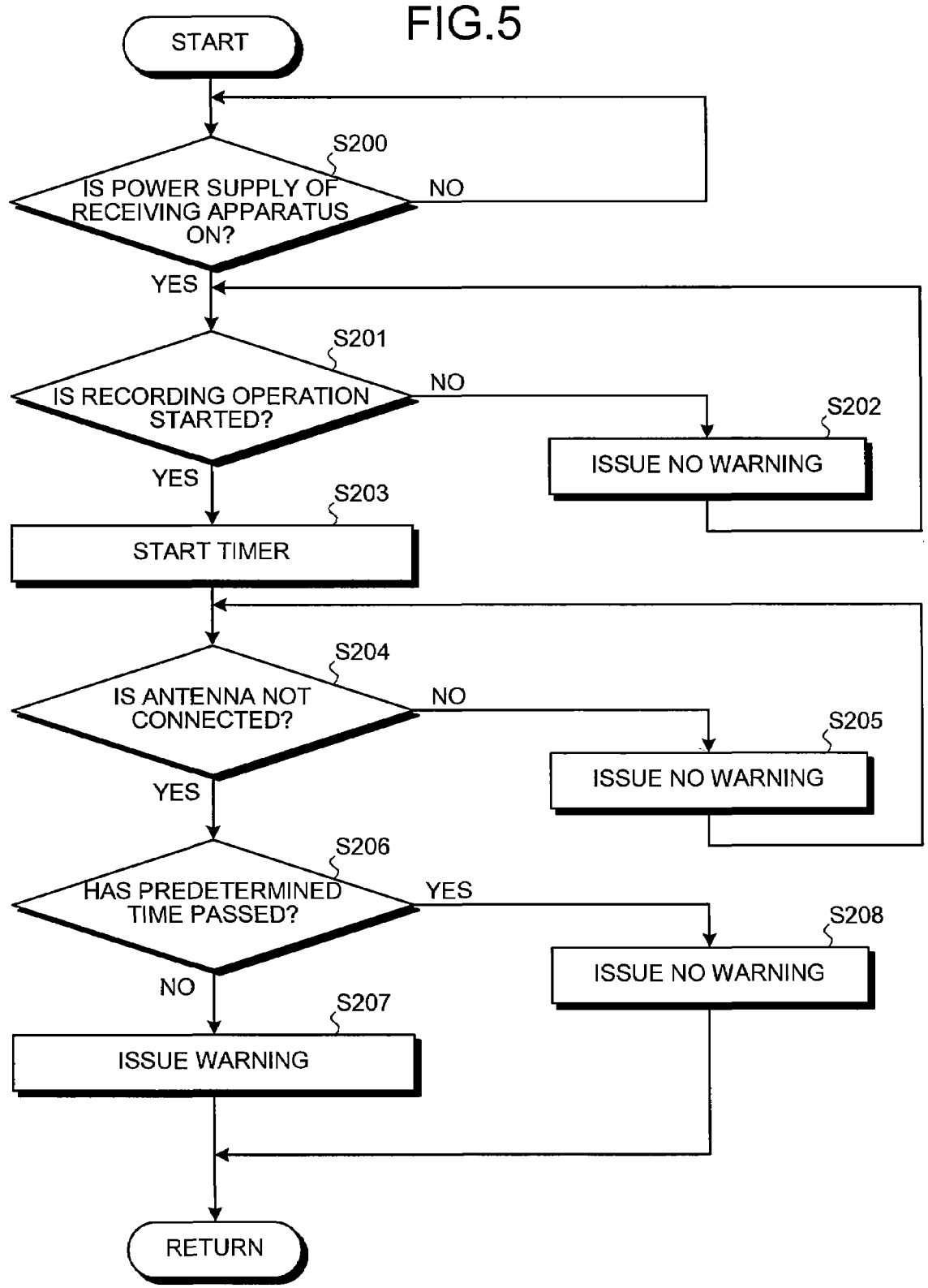
FIG. 5 is a schematic flowchart showing an example of warning control executed when an antenna according to a second embodiment of the present invention is detached.

A second embodiment of the present invention is explained with reference to FIG. 5. FIG. 5 is a schematic flowchart showing an example of warning control according to the present embodiment, executed when an antenna is detached. In the first embodiment, a warning is issued when the antenna detachment is detected after the recording operation is started. Therefore, a warning is issued when the antenna detachment is detected, before the power supply switch of the main receiving unit 2b is turned off, even after the capsule endoscope 3 is discharged from the subject 1 (at this stage, a body-cavity image cannot be acquired). However, at this stage, the body-cavity image data is already acquired, and it is not necessary to issue a warning even when the antenna is detached.

In the present embodiment, one examination using the capsule endoscope 3 ends after a constant time, for example, about eight hours, since the recording is started, and the capsule endoscope is discharged to the outside of the body cavity. Therefore, a timer 22 (see FIG. 3) is used to monitor a lapse time since the recording operation is started. Any warning is not issued even when the antenna is detached, after a lapse of a constant time, even after the recording is started.

This process is executed in a state that the power supply switch of the receiving apparatus 2 (the main receiving unit 2b) is turned on (step S200: Yes). Whether a recording operation is started is determined to determine whether the examination has been started (step S201). When the recording operation is not yet started (step S201: No), the state is normal even when the antenna is detached, and it is not necessary to warn the user. Therefore, the warning controller C2 controls the display unit 15 not to issue a warning (step S202).

On the other hand, when the recording operation has been started (step S201: Yes), the timer 22 is started at the time of starting the recording operation (step S203) It is determined whether the casing 20 of the antennas A1 to An is in the non-connection state (the antenna-detached state), by referencing a result of the detection executed by the connection state detector C3 (step S204). When the antenna detachment has not occurred (step S204: No), the state is normal, and no warning is issued to the user. Therefore, the warning controller C2 controls the display unit 15 not to issue a warning (step S205). When the antenna is detached (step S204: Yes), it is determined whether a predetermined time has passed since the recording operation is started (step S206). When a predetermined time has not passed yet (step S206: No), the examination is being continued, and the antenna is detached as the abnormal state. Therefore, the warning controller C2 controls the operation of the display unit 15 to display the warning of "Antenna is detached. Please connect it again." (step S207). With this arrangement, the user (the subject 1, the doctor, or the nurse) can promptly make proper response to make the connecting unit 19 of the main receiving unit 2b connect the casing 20 of the antennas A1 to An again, thereby suppressing data loss when the antenna is detached.

On the other hand, even when the antenna detachment has occurred (step S204: Yes), when a predetermined time has passed since the recording operation is started (step S206: Yes), the capsule endoscope 3 is already detached to the outside of the body cavity, and the acquisition of the body-cavity image data is not necessary. Therefore, no warning is issued to the user, and the warning controller C2 controls the display unit 15 not to display the warning (step S208).

Third Embodiment

Figure 6:
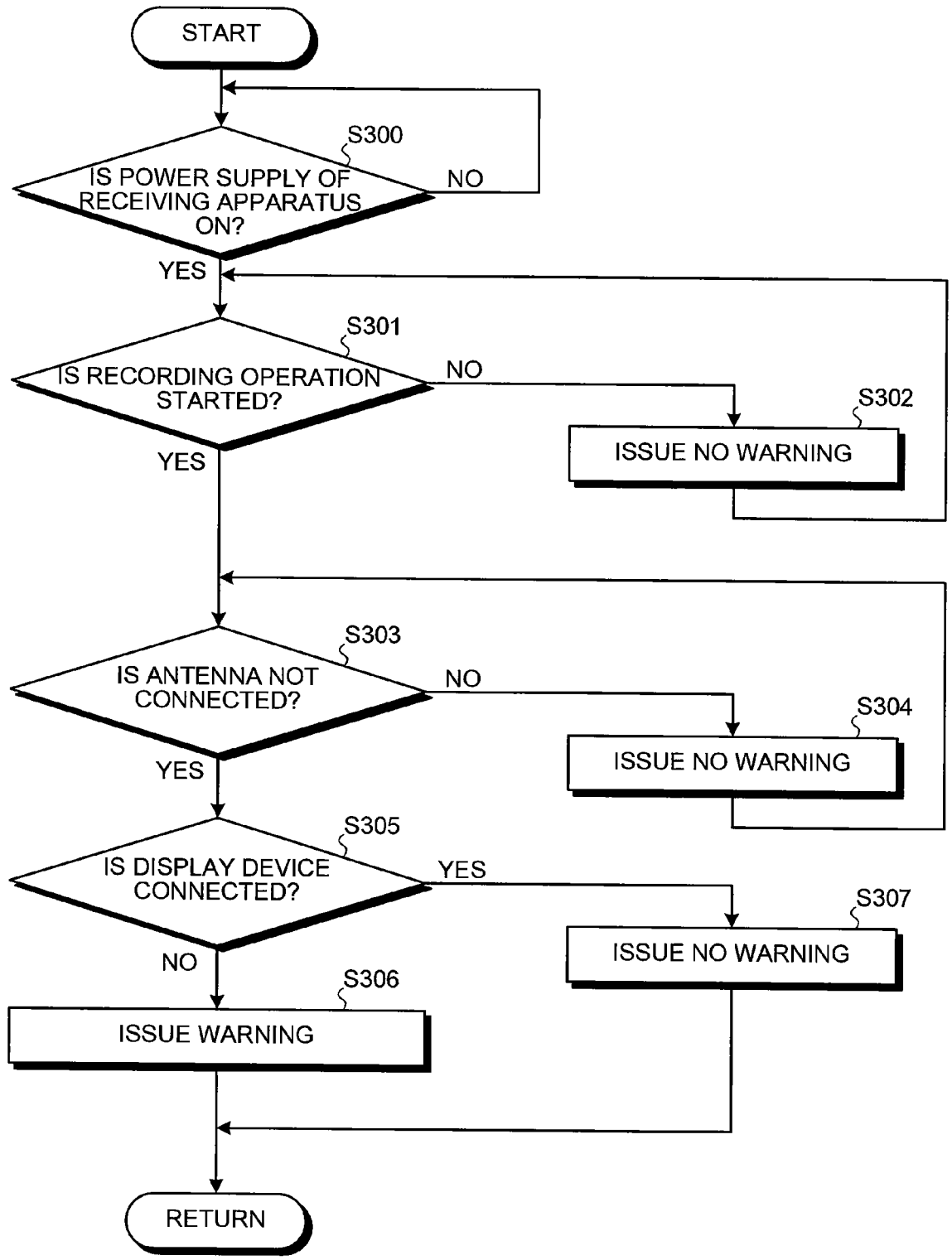
FIG. 6 is a schematic flowchart showing an example of warning control executed when an antenna according to a third embodiment of the present invention is detached.

A third embodiment of the present invention is explained with reference to FIG. 6. FIG. 6 is a schematic flowchart showing an example of warning control according to the present embodiment, executed when an antenna is detached. In the present embodiment, the main receiving unit 2b includes a built-in type recording medium such as a hard disk, in place of the portable recording medium 5. Data is delivered to the display device 4, by connecting the main receiving unit 2b to the display device 4.

In the first embodiment, a warning is issued when the antenna detachment is detected after the recording operation is started. When the main receiving unit 2b is connected to the display device 4 to transfer data after the examination ends, for example, the detachment of the antenna causes a warning to be issued when the power supply switch of the main receiving unit 2b is on. However, at this stage, the examination has already ended, and there is no need to issue a warning when the antenna is detached. On the contrary, it is necessary to facilitate the connection between the main receiving unit 2b and the display device 4, by detaching the casing 20 of the antennas A1 to An.

In the present embodiment, when the main receiving unit 2b and the display device 4 are connected to each other, any warning is not issued even when the antenna is detached. This process is executed in the state that the power supply switch of the receiving apparatus 2 (the main receiving unit 2b) is turned on (step S300: Yes). Next, whether a recording operation is started is determined to determine whether the examination has been started (step S301). When the recording operation is not yet started (step S301: No), the state is normal even when the antenna is detached, and it is not necessary to warn the user. Therefore, the warning controller C2 controls the display unit 15 not to issue a warning (step S302).

On the other hand, when the recording operation has been started (step S301: Yes), it is determined whether the casing 20 of the antennas A1 to An is in the non-connection state (the antenna-detached state), by referencing a result of the detection executed by the connection state detector C3 (step S303). When the antenna detachment has not occurred (step S303: No), the state is normal, and no warning is issued to the user. Therefore, the warning controller C2 controls the display unit 15 not to issue a warning (step S304). When the antenna is detached (step S303: Yes), it is determined whether the main receiving unit 2b is connected to the display device 4 (step S305). This state can be determined based on the state of a USB terminal that connects between the both. When the display device 4 is not connected (step S305: No), the examination is being continued, and the antenna is detached as the abnormal state. Therefore, the warning controller C2 controls the operation of the display unit 15 to display the warning of "Antenna is detached. Please connect it again." (step S306). With this arrangement, the user (the subject 1, the doctor, or the nurse) can promptly make proper response to make the connecting unit 19 of the main receiving unit 2b connect the casing 20 of the antennas A1 to An again, thereby suppressing data loss when the antenna is detached.

On the other hand, even when the antenna detachment has occurred (step S303: Yes), when the display device 4 is being connected (step S305: Yes), the examination has already ended, and there is no need to issue a warning to the user. Therefore, the warning controller C2 controls the display unit 15 not to issue a warning (step S307).

INDUSTRIAL APPLICABILITY

As described above, the receiving apparatus according to the present invention is useful when the antenna at the outside of the subject is used to receive a radio signal transmitted from the body-insertable apparatus such as the capsule endoscope inserted into the subject, and it is particularly useful when a detachable antenna is provided.

The invention claimed is:

1. A receiving apparatus comprising:
 an antenna that is detachably connected to a receiving apparatus main body, and receives a radio signal transmitted from a body-insertable apparatus;
 an operation start detector that detects a start of a recording operation following a reception of a radio signal transmitted from the body-insertable apparatus;
 a connection state detector that detects a state of connection of the antenna to the receiving apparatus main body;
 a warning unit that issues a warning to a user; and
 a controller that operates the warning unit when a non-connection of the antenna is detected after a recording operation is started.

2. The receiving apparatus according to claim 1, further comprising
 a measuring unit that measures a lapse time since the recording operation is started, wherein
 the controller operates the warning unit when a non-connection of the antenna is detected after the recording operation is started and before a predetermined time set in advance passes.

3. The receiving apparatus according to claim 1, further comprising
 an external-device connection detector that detects presence of a connection with an external data processor, wherein
 the controller operates the warning unit, when a non-connection of the antenna is detected in a state that the external data processor is not connected after the recording operation is started.

4. The receiving apparatus according to claim 1, wherein the warning unit issues a warning by displaying a warning on a display unit.

5. The receiving apparatus according to claim 1, wherein the warning unit issues a warning by lighting on or blinking a light-emitting element.

6. The receiving apparatus according to claim 1, wherein the warning unit issues a warning using a warning sound.

7. The receiving apparatus according to claim 1, wherein the warning unit issues a warning by vibrating the receiving apparatus main body.

8. The receiving apparatus according to claim 2, further comprising
 an external-device connection detector that detects presence of a connection with an external data processor, wherein
 the controller operates the warning unit, when a non-connection of the antenna is detected in a state that the external data processor is not connected after the recording operation is started.

9. The receiving apparatus according to claim 2, wherein the warning unit issues a warning by displaying a warning on a display unit.

10. The receiving apparatus according to claim 3, wherein the warning unit issues a warning by displaying a warning on a display unit.

11. The receiving apparatus according to claim 8, wherein the warning unit issues a warning by displaying a warning on a display unit.

12. The receiving apparatus according to claim 2, wherein the warning unit issues a warning by lighting on or blinking a light-emitting element.

13. The receiving apparatus according to claim 3, wherein the warning unit issues a warning by lighting on or blinking a light-emitting element.

14. The receiving apparatus according to claim 8, wherein the warning unit issues a warning by lighting on or blinking a light-emitting element.

15. The receiving apparatus according to claim 2, wherein the warning unit issues a warning using a warning sound.

16. The receiving apparatus according to claim 3, wherein the warning unit issues a warning using a warning sound.

17. The receiving apparatus according to claim 8, wherein the warning unit issues a warning using a warning sound.

18. The receiving apparatus according to claim 2, wherein the warning unit issues a warning by vibrating the receiving apparatus main body.

19. The receiving apparatus according to claim 3, wherein the warning unit issues a warning by vibrating the receiving apparatus main body.

20. The receiving apparatus according to claim 8, wherein the warning unit issues a warning by vibrating the receiving apparatus main body.

* * * * *